(12) United States Patent
Omura et al.

(10) Patent No.: US 7,973,147 B2
(45) Date of Patent: Jul. 5, 2011

(54) K04-0144 SUBSTANCE AND A PROCESS FOR PRODUCTION THEREOF

(75) Inventors: Satoshi Omura, Tokyo (JP); Hiroshi Tomoda, Tokyo (JP); Yong-pil Kim, Chiba (JP); Hideaki Hanaki, Kanagawa (JP); Atsuko Matsumoto, Tokyo (JP); Yoko Takahashi, Tokyo (JP)

(73) Assignee: The Kitasato Institute, Tokyo (JP)

( * ) Notice: Subject to any disclaimer, the term of this patent is extended or adjusted under 35 U.S.C. 154(b) by 179 days.

(21) Appl. No.: 12/084,878

(22) PCT Filed: May 16, 2006

(86) PCT No.: PCT/JP2006/310091
§ 371 (c)(1),
(2), (4) Date: Aug. 6, 2008

(87) PCT Pub. No.: WO2007/132537
PCT Pub. Date: Nov. 22, 2007

(65) Prior Publication Data
US 2009/0130717 A1    May 21, 2009

(51) Int. Cl.
*C07H 15/20*  (2006.01)
*C07H 15/22*  (2006.01)
*C07C 61/12*  (2006.01)
(52) U.S. Cl. .................. 536/13.4; 536/14; 562/501
(58) Field of Classification Search .................. None
See application file for complete search history.

(56) References Cited

FOREIGN PATENT DOCUMENTS
JP    9-509677 A    9/1997

OTHER PUBLICATIONS

Donnerstag et al., "A structurally and biogenetically interesting moenomycin antibiotic," Tetrahedron, vol. 51, No. 7, 1995, pp. 1931-1940.
Hasegawa, "MRSA," pp. 264-273.

*Primary Examiner* — Delia M Ramirez
*Assistant Examiner* — Md. Younus Meah
(74) *Attorney, Agent, or Firm* — Birch, Stewart, Kolasch & Birch, LLP (57) ABSTRACT

A microorganism represented by a strain K04-0144 belonging to *Streptomyces* sp. having ability to produce K04-0144 substance is cultured in the medium, and the isolated K04-0144A substance, K04-0144B substance and K04-0144C substance therefrom have strong antibacterial activities against Gram-positive bacteria including methicillin-resistant *Streptococcus aureus* (MRSA), consequently these are useful as the therapeutic agents for infectious disease caused by MRSA as well as infectious diseases caused by multidrug including β-lactam antibiotics resistant bacteria. Further, similarly, since the novel K04-0144D substance isolated from the cultured liquid has the action for enhancing the effect of β-lactam antibiotics, which are utilized as the antibacterial agents, in combination with them, it is useful as the therapeutic agent for infectious diseases caused by methicillin-resistant *Staphylococcus aureus* (MRSA) and multidrug including β-lactam antibiotics resistant bacteria.

5 Claims, 8 Drawing Sheets

K04-0144 SUBSTANCE AND A PROCESS FOR PRODUCTION THEREOF

TECHNICAL FIELD

The present invention relates to novel K04-0144 substance including any of K04-0144A substance, K04-0144B substance and K04-0144C substance which exhibit antimicrobial action against various bacteria including methicillin-resistant *Staphylococcus aureus* (MRSA), and K04-0144D substance which exhibits increasing anti-MRSA activity in combination with β-lactam antibiotics, and a process for production thereof.

BACKGROUND ART

*Staphylococcus aureus* is an indigenous Gram positive bacterium on the body surface such as the skin and the gastrointestinal surface of the human and animals, and is harmless to the healthy humans, but in the immune-compromised cases such as postsurgical patients, new born infants and elderly persons, they develop various severe infectious diseases such as including from cutaneous soft tissue infection, for example suppurative conditions accompanied by incised wound or penetrating wound to pneumonia, peritonitis, sepsis, cerebral meningitis, and in addition thereto, food poisoning, shock syndrome and enteritis caused by enterotoxin and toxic shock syndrome toxin-1. There are not negligible severe cases and in worst cases cause to death. Recently, methicillin-resistant *Staphylococcus aureus* (MRSA) is recognized as social problem as a cause for causative microorganisms of in-hospital infection. This pathogenic microorganism is resistant against various drugs such as β-lactam antibiotics, consequently glycopeptide series antibiotic, vancomycin, and aminoglycoside series antibiotic arbekacin are used for treatment of MRSA infection at present. Other antibiotics recently developed such as quinupristin.delfopristin mixture and oxazolidinone antibiotic, linezolid are known.

Vancomycin and arbekacin presently used as the effective antibiotics against MRSA are known to exhibit side effects such as hearing impairment caused by eight cranial nerve disorder. Further, the glycopeptide antibiotic induces side effects such as shock, nephrotoxicity and red man syndrome, and when it is clinically administered, careful administration such as performing blood level monitoring is required. In addition to the multiply-resistant MRSA, low sensitive bacteria against major curative drug vancomycin are reported. Consequently, appearance of novel antibiotics and development of new therapeutic methods are demanded. Actually as the new therapeutic method, a combination therapy with β-lactam antibiotics or β-lactam antibiotic and other antibiotic having different mode of action is on going (Hiromi Hasegawa et al. "Science of antibiotic administration, pp. 264-273, 1998). Further, a substance which does not exhibit antimicrobial activity by itself but has an action to recover or activate an efficacy of β-lactam antibiotics is reported. For example, tea extract or its active fractions (polyphenol compounds) disclosed in the published Japanese translation of PCT international publication for patent application Hei 9-509677 or stemphones (PCT/JP2006/305625) can be mentioned.

Problem To Be Solved By The Invention

Considering such the background, it is important to provide novel antibiotics with new structure exhibiting antibacterial activity against MRSA. Further, drugs enhancing activity of β-lactam antibiotics against MRSA are expected to reduce dose level of β-lactam antibiotics and to decrease frequency of appearance of resistant bacteria as a result of reduction of dosing period. Further at the same time, overcoming the drug resistance is expected by combining two drugs with different mode of action.

An object of the present invention is to provide novel therapeutic drugs for MRSA infection and infectious diseases caused by multidrug-resistant microorganisms including β-lactam antibiotics resistance.

Means For Solving Problem

The present inventors have extensively studied a way to explore compounds exhibiting antimicrobial activities against MRSA or compounds enhancing activities of β-lactam antibiotics targeting to the metabolites produced by microorganisms, and found that substances exhibiting the objective activities were produced in a culture fluid of *Streptomyces* strain K04-0144 which was newly isolated from soil. Subsequently, substances showing the objective activities were isolated and purified from the cultured mass and three types of anti-MRSA antibiotics and a compound enhancing activities of β-lactam antibiotics could be obtained. Since the substances with such chemical structures were not known previously, the anti-MRSA antibiotics were designated as K04-0144A substance, K04-0144B substance and K04-0144C substance, and the active substance with enhancing activities of β-lactam antibiotics was designated as K04-0144D substance. Further, any of these substances was totally designated as K04-0144 substance.

The present invention has been completed according to such knowledge and is K04-0144 substance comprised any of:

K04-0144A substance having the following formula [I]

K04-0144B substance having the following formula [II]

K04-0144C substance having the following formula [III]

and
K04-0144D substance having the following formula [IV]

[IV]

The present invention is a process for production of novel K04-0144 substance comprising culturing a microorganism belonging to genus *Streptomyces* and having ability to produce substance in a medium, accumulating K04-0144 substance in the cultured medium, and isolating K04-0144 substance from the cultured mass.

The present invention is a microorganism *Streptomyces* sp. K04-0144 (NITE BP-107).

The strain used for production of novel K04-0144 substance represented by the formula [I], [II], [III] and [IV] hereinabove can be mentioned as an example such the strain as *Streptomyces* sp. K04-0144, which was newly isolated by the present inventors from the soil of Ishigaki-island, Okinawa Pref., Japan.

Taxonomical properties of the present strain are as follows.
(I) Morphological Properties Vegetative mycelia show good growth on various agar media and no fragmentation is observed. Aerial mycelia grow well on yeast extract-malt extract agar and glycerol-asparagine agar, and are white to gray color. On microscopic observation, chains of 20 spores or more are observed on the aerial mycelia, and their forms are spiral. Size of spores is cylindrical with about 1.0×1.0 μm. Surface of spores is smooth. Sclerotia, sporangia and zoospores are not observed.

(II) Characteristics on Various Media

Cultural properties of this strain observed according to the method of E. B. Shirling and D. Gottlieb (International Journal of Systematic Bacteriology, 16: 313, 1966) are shown in the following table. Color is determined by the standard color using Color Harmony Manual, 4th Ed. (Container Corp. of America, Chicago, 1958), and is shown by color name with its code in parentheses. The lists are, if not specified, results of observation at 27° C. for 2nd weeks on various media.

Cultural Characteristics:

Sucrose-nitrate Agar

| Growth | Moderate, Ivory (2db) |
|---|---|
| Reverse side | Ivory (2db) |
| Aerial mycelia | Poor, White (a)-Dark Covert gray (2ih) |
| Soluble pigment | None |

Glucose-asparagine Agar

| Growth | Good, Light ivory (2ca)-Canary yellow (1ea) |
|---|---|
| Reverse side | Light olive drab (1li)-Pale yellow (1ca) |
| Aerial mycelia | Poor, White (a)-Dark Covert gray (2ih) |
| Soluble pigment | None |

Glycerol-asparagine Agar (ISP)

| Growth | Good, Light mustard tan (2ie) |
|---|---|
| Reverse side | Light mustard tan (2ie)-No name (24½ ml) |
| Aerial mycelia | Abundant, White (a)-Pearl gray (13cb) |
| Soluble pigment | None |

Starch-inorganic Salt Agar (ISP)

| Growth | Good, Light ivory (2ca) |
|---|---|
| Reverse side | Light ivory (2ca)-Dark Covert gray (2ih) |
| Aerial mycelia | Moderate, Oyster white (b) |
| Soluble pigment | None |

Tyrosine Agar (ISP)

| Growth | Good, Bamboo (2gc)-Dark olive gray (1ml) |
|---|---|
| Reverse side | Bamboo (2gc)-Dark olive gray (1ml) |
| Aerial mycelia | Moderate, White (a)-Light gray (c) |
| Soluble pigment | None |

Oatmeal Agar (ISP)

| Growth | Good, Pale yellow (1ca) |
|---|---|
| Reverse side | Cream (1½ ca)-Olive gray (1ig) |
| Aerial mycelia | Moderate, White (a)-Dark covert gray (2ih) |
| Soluble pigment | None |

Yeast Extract-malt Extract Agar (ISP)

| Growth | Good, Light mustard tan (2ie) |
|---|---|
| Reverse side | Light olive drab (1li) |
| Aerial mycelia | Abundant, White (a)-Gray (f) |
| Soluble pigment | None |

Nutrient Agar

| Growth | Good, Light ivory (2ca) |
|---|---|
| Reverse side | Cream (1½ ca) |
| Aerial mycelia | Poor, White (a) |
| Soluble pigment | None |

Peptone-yeast Extract-iron Agar (ISP)

| Growth | Good, Light ivory (2ca) |
|---|---|
| Reverse side | Bamboo (2gc) |
| Aerial mycelia | None |
| Soluble pigment | None |

Glucose-nitrate Agar

| Growth | Poor, Pearl pink (3ca)-Bamboo (2gc) |
|---|---|
| Reverse side | Light ivory (2ca) |
| Aerial mycelia | Poor, White (a) |
| Soluble pigment | None |

Glycerol-calcium Malate Agar

| | |
|---|---|
| Growth | Good, Alabaster tint (13ba)-Pale yellow (1ca) |
| Reverse side | Alabaster tint (13ba) |
| Aerial mycelia | Poor, White (a) |
| Soluble pigment | None |

Glucose-peptone Agar

| | |
|---|---|
| Growth | Moderate, Light mustard tan (2ie) |
| Reverse side | Bamboo (2gc) |
| Aerial mycelia | None |
| Soluble pigment | None |

(III) Physiological Properties

| | |
|---|---|
| (1) Formation of melanin pigment | |
| (a) Tyrosine agar | Negative |
| (b) Peptone-yeast extract-iron agar | Negative |
| (c) Tryptone-yeast liquid | Negative |
| (d) Simple gelatin medium | Negative |
| (2) Nitrate reduction | Negative |
| (3) Liquefaction of gelatin (at 21-23° C.) (simple gelatin medium) | Negative |
| (4) Hydrolysis of starch | Positive |
| (5) Coagulation of defatted milk (at 37° C.) | Positive |
| (6) Peptonization of defatted milk (at 37° C.) | Positive |
| (7) Growth temperature | 12-42° C. |
| (8) Utilization of carbon sources (Pridham - Gottlieb medium) | |
| Utilized: | D-glucose, melibiose, D-mannitol, L-Rhamnose |
| Slightly utilized: | L-arabinose, D-xylose, raffinose, D-fructose, sucrose |
| (9) Decomposition of cellulose | Negative |

(IV) Chemotaxonomical properties

Diaminopimelic acid of cell wall is LL-type and major menaquinones are MK-9($H_6$) and MK-9($H_8$).

(V) Conclusion

Taxonomical properties of the present strain are summarized as follows. Diaminopimelic acid in the cell wall is LL-type, and major menaquinones are MK-9($H_6$) and MK-9 ($H_8$). Forms of spore chain are spiral with forming long spore chain and surface of spore is smooth. The color of vegetative mycelia is brown. The aerial mass color is white to gray. No melanin pigment formation is observed.

From these results, the strain is referred to belong genus *Streptomyces* according to Bergey's Manual of Systematic Bacteriology, Vol. 4, 1989.

International Deposition of Microorganism

The present strain was deposited as *Streptomyces* sp. K04-0144 based on the Budapest Treaty on the International Recognition of the Deposit of Microorganisms for the Purposes of Patent Procedure in the International Administrative Agency, National Institute of Technology and Evaluation Patent Microorganisms Depositary (NPMD), 1-5-8 Kazusa-kamatari, Kisarazu-shi, Chiba-ken, 292-0818 Japan. Date of deposition is Jun. 30, 2005, and accession number is NITE BP-107.

Physico-chemical Properties:

Physico-chemical properties of K04-0144 substance of the present invention are explained hereinbelow.

Figure 1:
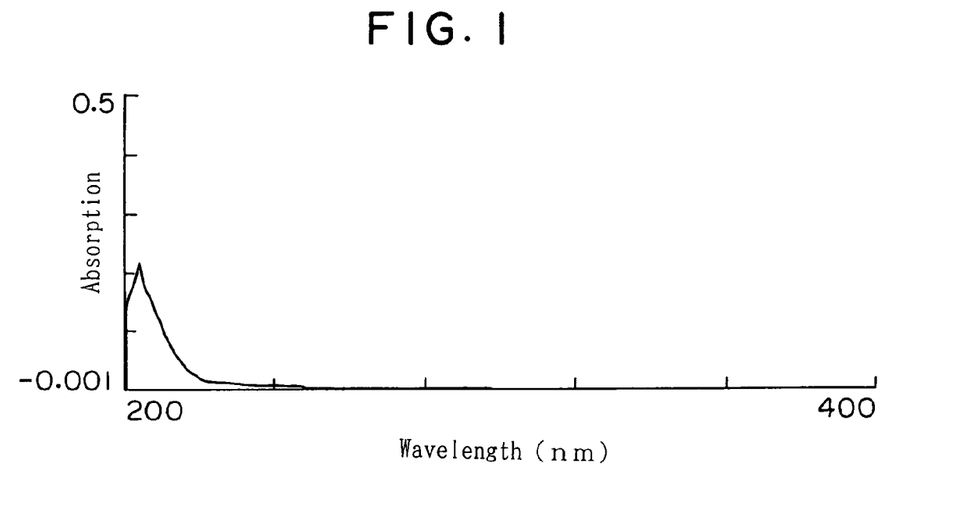
FIG. 1: UV spectrum (in methanol) of K04-0144A substance
Figure 2:
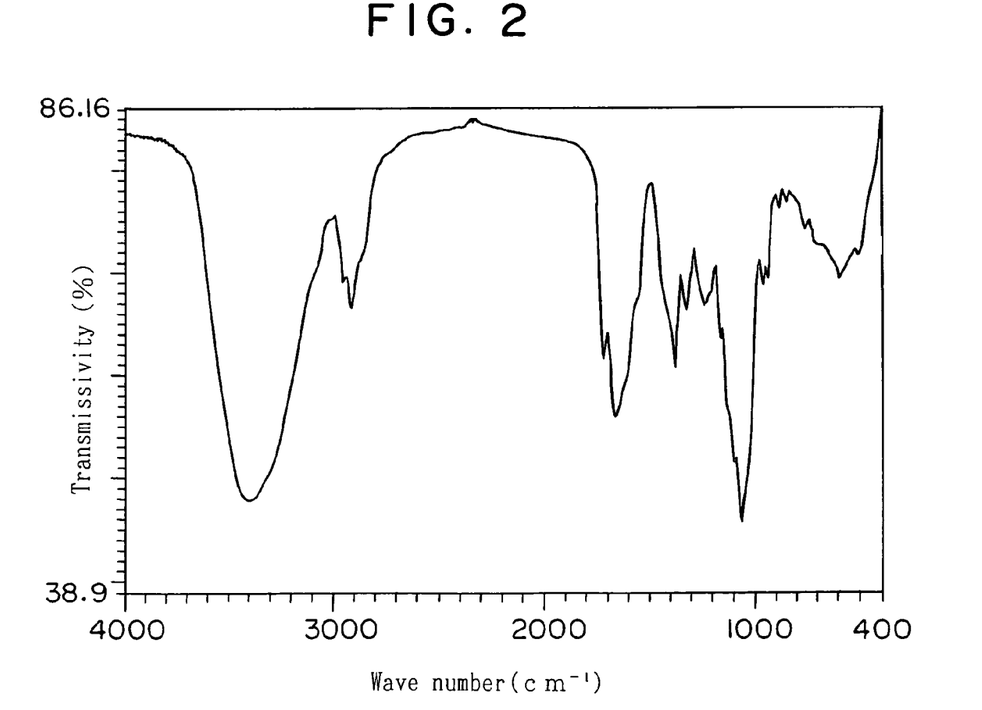
FIG. 2: IR spectrum (KBr) of K04-0144A substance
Figure 3:
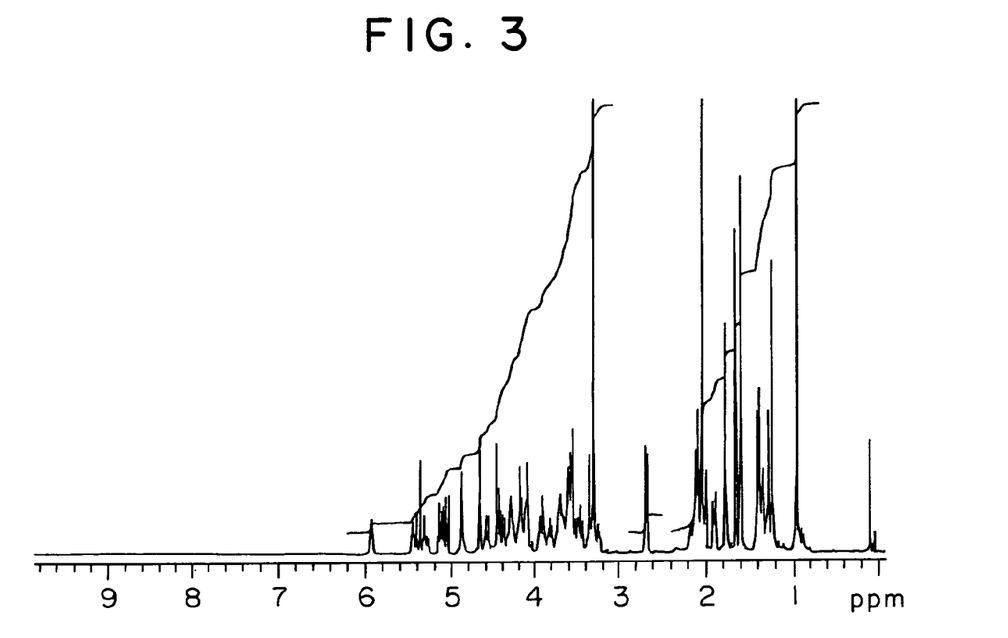
FIG. 3: Proton NMR spectrum (in deuterated methanol) of K04-0144A substance
Figure 4:
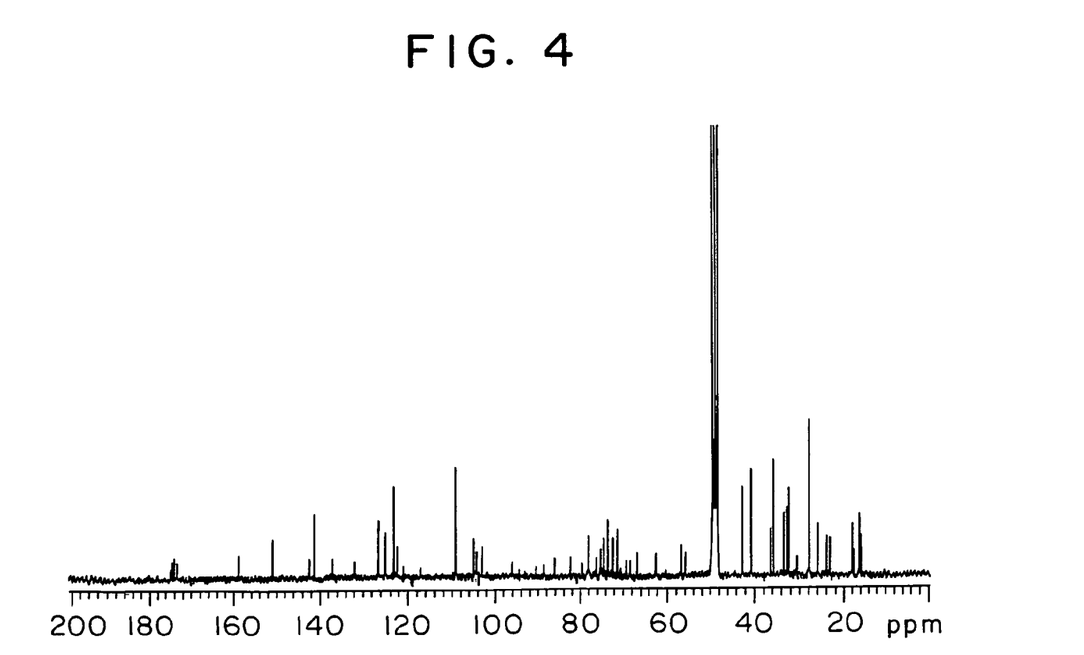
FIG. 4: Carbon NMR spectrum (in deuterated methanol) of K04-0144A substance

1. K04-0144A substance
(1) Property: white powder
(2) Molecular formula: $C_{64}H_{103}N_4O_{33}P$
HR Neg. ESI-MS (m/z) [M-H]⁻: Calculated 1485.6206. Experimental 1485.6164
(3) Molecular weight: 1487
Neg. ESI-MS (m/z) [M-H]⁻: A value 1485 was observed.
(4) UV spectrum: in methanol, FIG. 1, end absorption
(5) IR spectrum: KBr, FIG. 2,
Specific absorptions vmax at 3299, 2960, 1722, 1673, 1068 $cm^{-1}$ were observed.
(6) Specific rotation: $[\alpha]_D^{24}$=+6.7° (c=0.1, MeOH)
(7) Solubility in solvent:
Soluble in methanol and water DMSO
Insoluble in acetone, chloroform and hexane
(8) Proton and carbon NMR spectra: In deuterated methanol, using Varian Inc. 400 MHz NMR spectrometer, proton NMR spectrum is shown in FIG. 3, and carbon NMR spectrum is shown in FIG. 4. Chemical shifts (ppm) of hydrogen and carbon are shown as follows.

$\delta_H$: 0.97 (6H), 1.26 (3H), 1.37 (2H), 1.41 (3H), 1.60 (3H), 1.62 (3H), 1.67 (3H), 1.78 (3H), 1.91 (2H), 2.01 (2H), 2.04 (3H), 2.05 (3H), 2.10 (4H), 2.13 (1H), 2.17 (1H), 2.70 (1H), 3.25 (1H), 3.31 (2H), 3.35 (1H), 3.46 (1H), 3.51 (1H), 3.55 (3H), 3.60 (3H), 3.67 (1H), 3.70 (1H), 3.71 (1H), 3.81 (1H), 3.90 (1H), 3.93 (1H), 4.09 (1H), 4.11 (1H), 4.15 (1H), 4.18 (2H), 4.28 (1H), 4.29 (1H), 4.38 (1H), 4.42 (1H), 4.45 (1H), 4.47 (1H), 4.57 (1H), 4.66 (1H), 4.67 (1H), 5.06 (1H), 5.10 (1H), 5.14 (1H), 5.29 (1H), 5.38 (1H), 5.45 (1H), 5.93 (1H) ppm $\delta_C$: 16.1, 16.4, 17.8, 18.0, 23.3, 23.5, 24.0, 26.0, 27.7, 27.9, 27.9, 32.4, 32.7, 33.5, 35.9, 36.5, 40.9, 42.9, 55.7, 56.9, 62.5, 66.9, 68.5, 69.4, 71.6, 71.6, 72.2, 72.6, 73.8, 73.8, 74.0, 74.1, 74.7, 75.0, 75.2, 75.4, 76.4, 78.0, 78.2, 78.3, 79.7, 82.4, 86.1, 96.2, 103.2, 104.3, 104.7, 105.1, 109.3, 122.7, 123.5, 125.4, 126.8, 132.2, 137.4, 141.6, 142.6, 151.1, 159.2, 173.5, 173.8, 174.2, 174.6, 175.1 ppm As a result of detailed examination of various physico-chemical properties and spectral data of K01-0144A substance, K01-0144A substance was determined to have the chemical structure [I] as shown hereinbefore.

Figure 5:
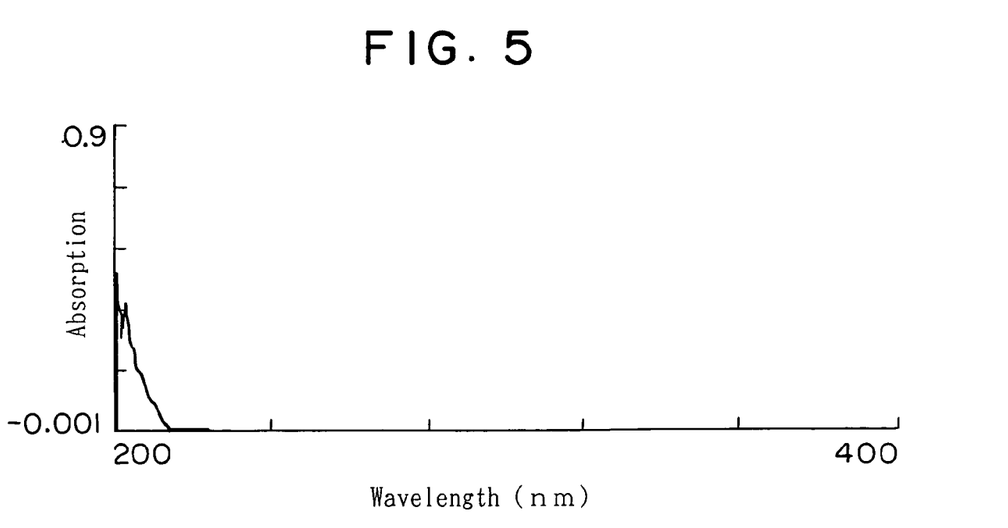
FIG. 5: UV spectrum (in methanol) of K04-0144B substance
Figure 6:
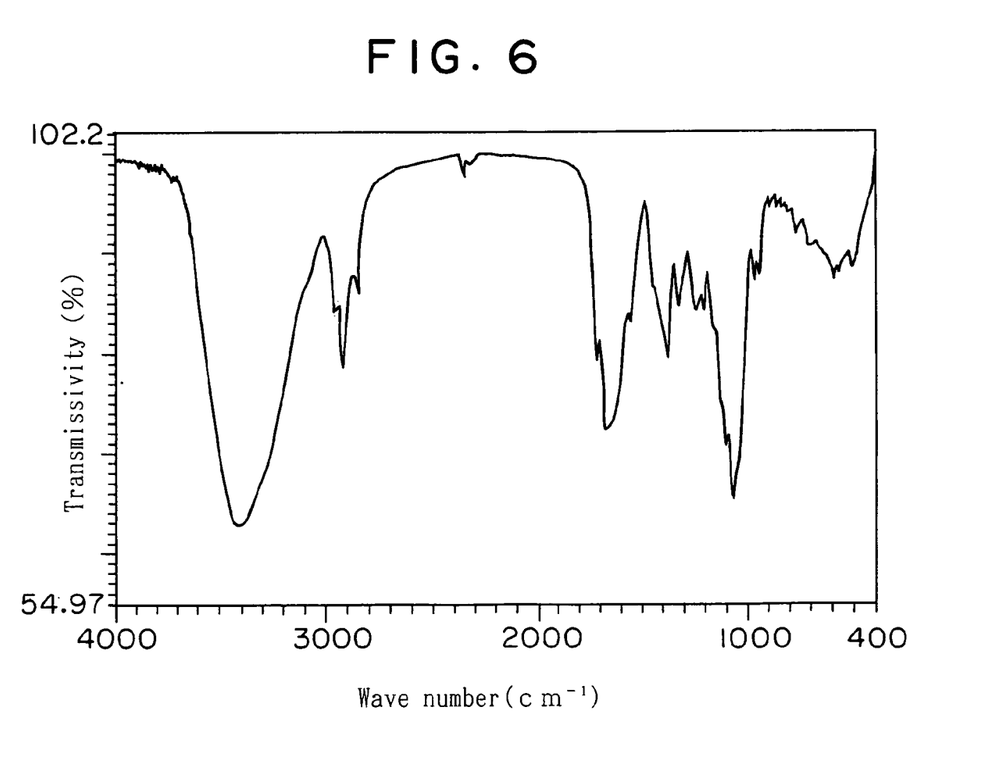
FIG. 6: IR spectrum (KBr) of K04-0144B substance
Figure 7:
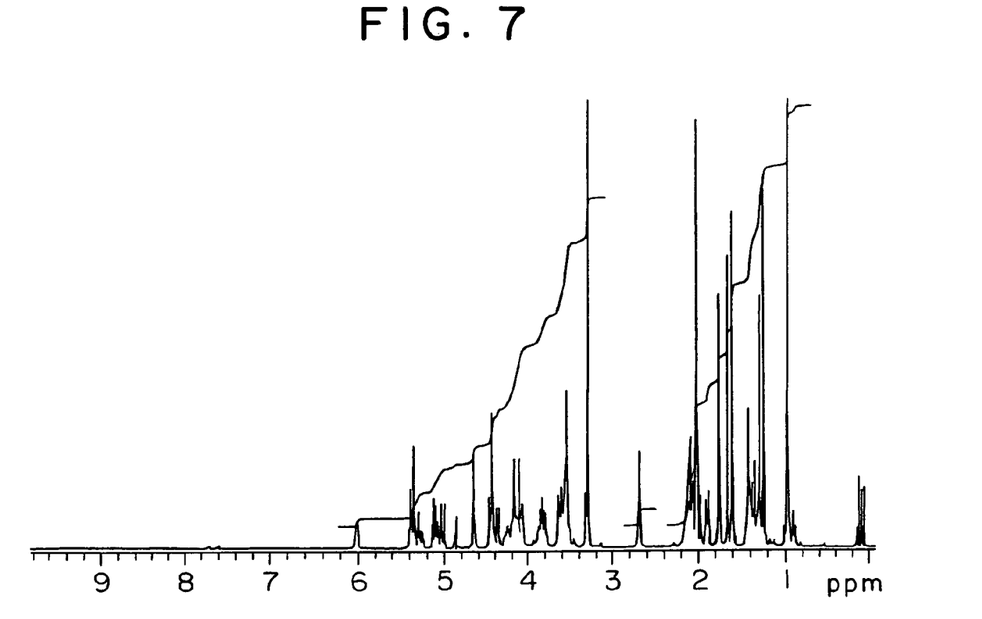
FIG. 7: Proton NMR spectrum (in deuterated methanol) of K04-0144B substance
Figure 8:
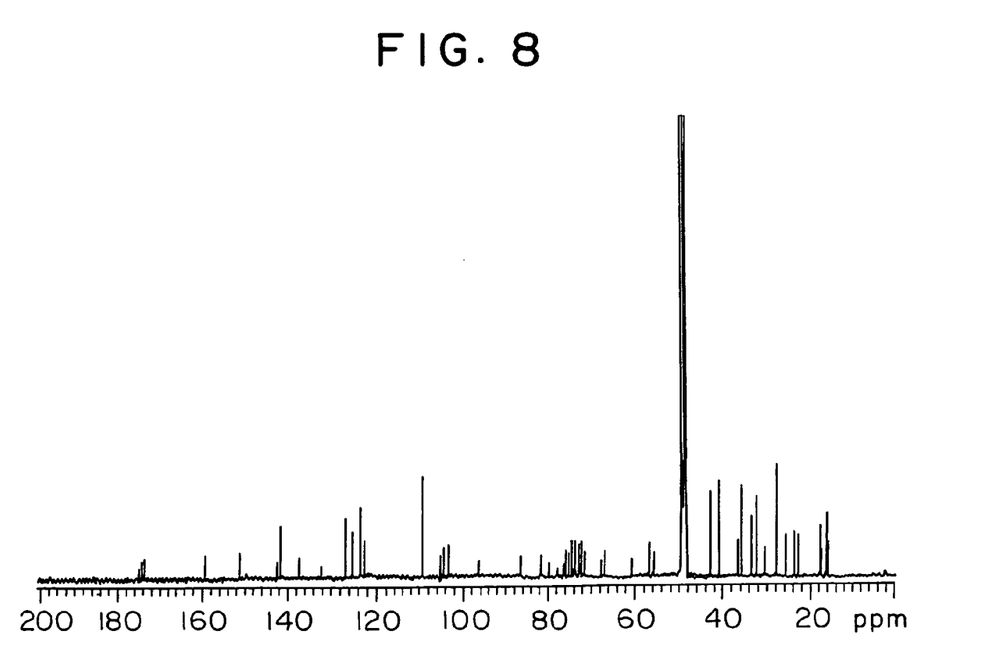
FIG. 8: Carbon NMR spectrum (in deuterated methanol) of K04-0144B substance

2. K04-0144B Substance
(1) Property: white powder
(2) Molecular formula: $C_{58}H_{93}N_4O_{28}P$
HR Neg. ESI-MS (m/z) [M-H]⁻: Calculated 1323.5656. Experimental 1323.5636
(3) Molecular weight: 1325
Neg. ESI-MS (m/z) [M-H]⁻: A value 1323 was observed.
(4) UV spectrum: in methanol, FIG. 5, end absorption
(5) IR spectrum: KBr, FIG. 6,
Specific absorptions vmax at 3299, 2923, 1716, 1675, 1068 $cm^1$ were observed.
(6) Specific rotation: $[\alpha]_D^{24}$=+4.0° (c=0.1, MeOH)
(7) Solubility in solvent:
Soluble in water, methanol and dimethyl sulfoxide
Insoluble in acetone, chloroform and n-hexane
(8) Proton and carbon NMR spectra: In deuterated methanol, using Varian Inc. 400 MHz NMR spectrometer, proton NMR spectrum is shown in FIG. 7, and carbon NMR spectrum is shown in FIG. 8. Chemical shifts (ppm) of hydrogen and carbon are shown as follows.

$\delta_H$: 0.97 (6H), 1.26 (3H), 1.38 (2H), 1.42 (3H), 1.60 (3H), 1.61 (3H), 1.67 (3H), 1.77 (3H), 1.91 (2H), 2.02 (3H), 2.03 (5H), 2.10 (4H), 2.14 (2H), 2.70 (2H), 3.31 (1H), 3.33 (1H), 3.54 (1H), 3.56 (2H), 3.58 (1H), 3.62 (1H), 3.64 (3H), 3.82 (1H), 3.84 (1H), 3.88 (1H), 4.08 (1H), 4.12 (1H), 4.13 (1H), 4.16 (1H), 4.17 (1H), 4.18 (1H), 4.26 (1H), 4.37 (1H), 4.44 (1H), 4.45 (1H), 4.47 (1H), 4.66 (1H), 4.67 (1H), 5.04 (1H), 5.10 (1H), 5.14 (1H), 5.29 (1H), 5.38 (1H), 5.39 (1H), 6.04 (1H) ppm $\delta_c$: 16.1, 16.3, 17.8, 18.0, 23.1, 23.3, 24.0, 26.0, 27.7, 27.8, 27.9, 32.4, 32.7, 33.4, 36.0, 36.5, 40.9, 42.9, 55.9, 56.7, 60.8, 67.0, 67.7, 71.6, 72.1, 72.6, 73.7, 73.8, 73.9, 74.1, 74.6, 75.1, 76.0, 76.3, 77.9, 79.9, 81.5, 86.4, 96.5, 103.4, 104.6, 105.2, 109.3, 122.8, 123.5, 125.4, 126.8, 132.2, 137.4, 141.7, 142.4, 151.1, 159.2, 173.2, 173.7, 174.1, 174.7, 174.9 ppm As a result of detailed examination of various physico-chemical properties and spectral data of K01-0144B substance, K01-0144B substance was determined to have the chemical structure [II] as shown hereinbefore.

Figure 9:
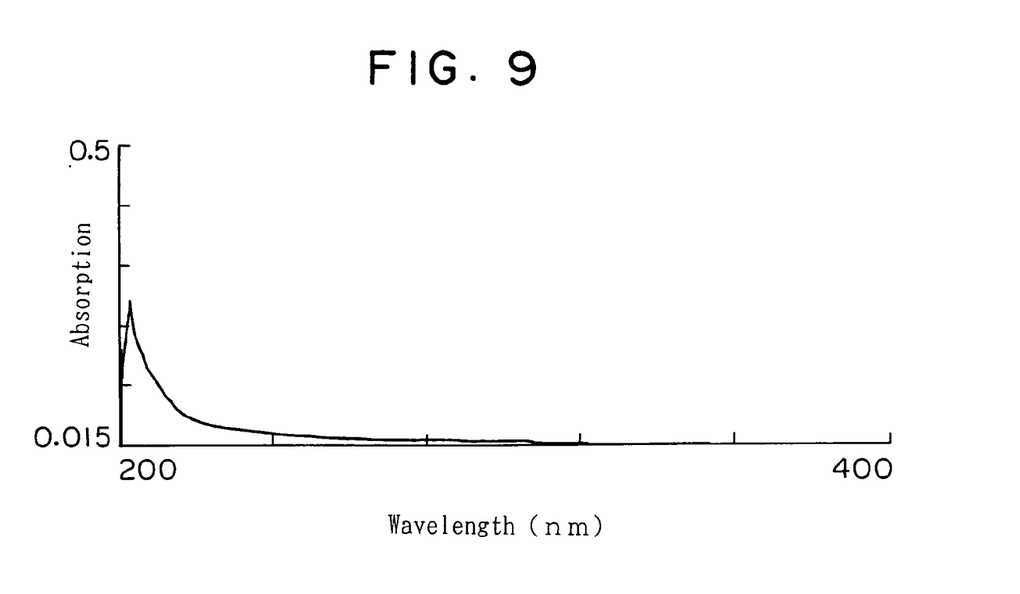
FIG. 9: UV spectrum (in methanol) of K04-0144C substance
Figure 10:
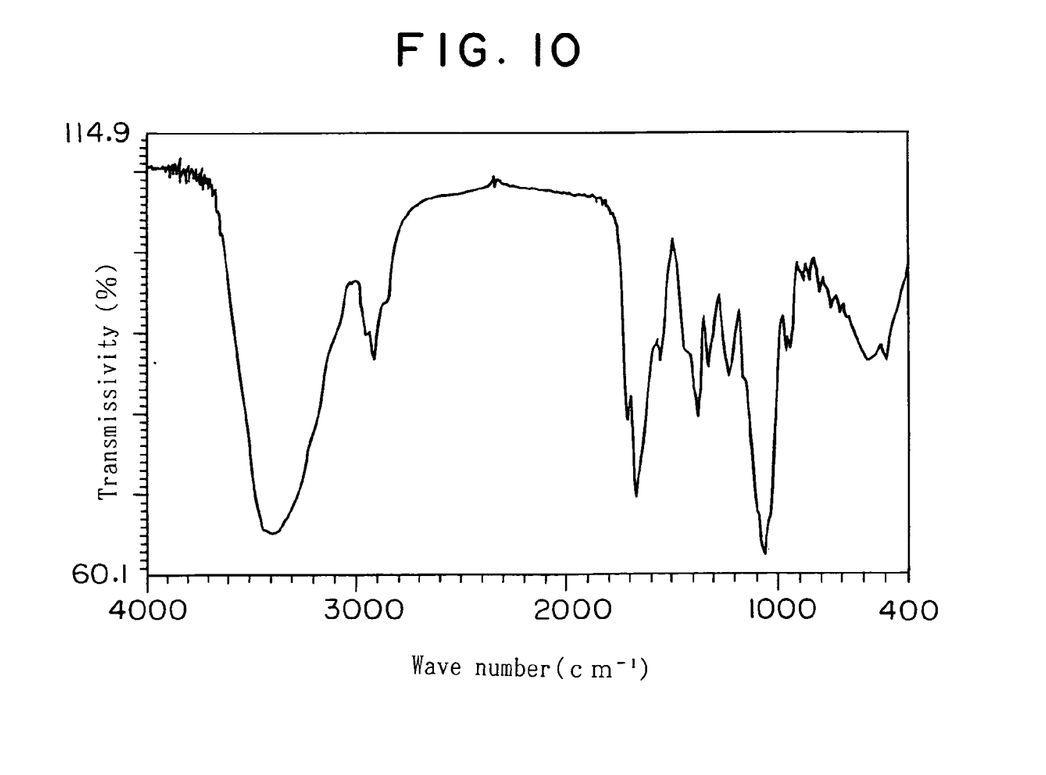
FIG. 10: IR spectrum (KBr) of K04-0144C substance
Figure 11:
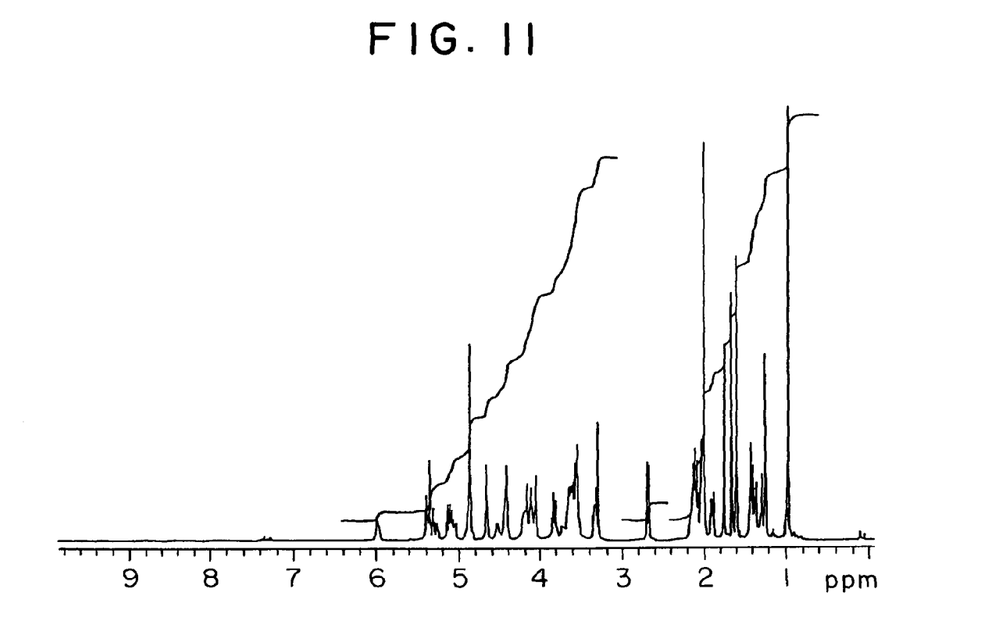
FIG. 11: Proton NMR spectrum (in deuterated methanol) of K04-0144C substance
Figure 12:
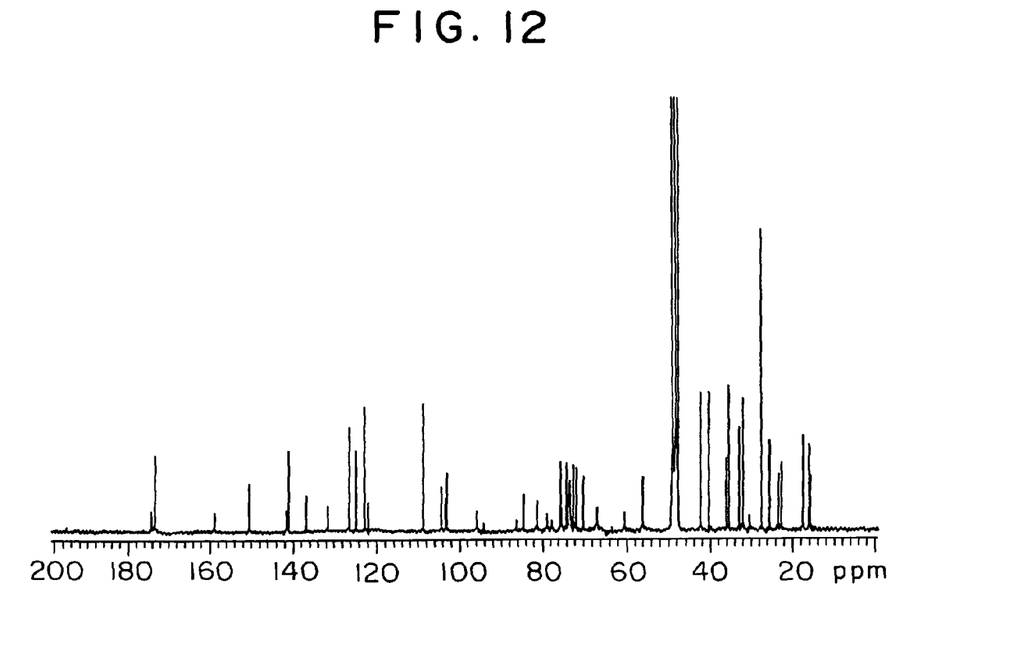
FIG. 12: Carbon NMR spectrum (in deuterated methanol) of K04-0144C substance

3. K04-0144C substance
(1) Property: white powder
(2) Molecular formula: $C_{58}H_{94}N_5O_{27}P$
HR Nef. ESI-MS (m/z) [M-H]$^-$: Calculated 1322.5859. Experimental 1322.5795
(3) Molecular weight: 1324
Neg. ESI-MS (m/z) [M-H]$^-$: A value 1323 was observed
(4) UV spectrum: in methanol, FIG. 9, end absorption
(5) IR spectrum: KBr, FIG. 10,
Specific absorptions vmax at 3400, 2925, 1677, 1648 cm$^{-1}$ were observed.
(6) Specific rotation: $[\alpha]_D^{24}$=+3.7° (c=0.1, MeOH)
(7) Solubility in solvent:
Soluble in water, methanol and dimethyl sulfoxide
Insoluble in acetone, chloroform and n-hexane
(8) Proton and carbon NMR spectra: In deuterated methanol, using Varian Inc. 400 MHz NMR spectrometer, proton NMR spectrum is shown in FIG. 11, and carbon NMR spectrum is shown in FIG. 12. Chemical shifts (ppm) of hydrogen and carbon are shown as follows.
$\delta_H$: 0.97 (6H), 1.25 (3H), 1.38 (2H), 1.42 (3H), 1.60 (3H), 1.61 (3H), 1.67 (3H), 1.76 (3H), 1.91 (2H), 2.01 (6H), 2.04 (2H), 2.09 (2H), 2.11 (2H), 2.14 (2H), 2.70 (2H), 3.34 (2H), 3.56 (4H), 3.64 (4H), 3.72 (1H), 3.83 (1H), 3.84 (1H), 4.06 (1H), 4.11 (3H), 4.17 (1H), 4.21 (2H), 4.42 (1H), 4.44 (1H), 4.46 (1H), 4.54 (1H), 4.66 (1H), 4.68 (1H), 5.07 (1H), 5.11 (1H), 5.14 (1H), 5.29 (1H), 5.38 (2H), 5.99 (1H) ppm
$\delta_c$: 16.1, 16.4, 17.8, 17.9, 23.1, 23.3, 23.9, 26.0, 27.7, 27.9, 27.9, 32.3, 32.6, 33.4, 36.0, 36.5, 40.9, 42.9, 56.5, 56.7, 61.0, 67.2, 67.6, 70.7, 72.3, 72.8, 73.5, 73.7, 73.9, 74.0, 74.4, 75.7, 76.0, 76.0, 78.3, 79.4, 81.6, 85.1, 96.2, 103.5, 103.9, 104.9, 109.3, 122.6, 123.5, 125.4, 126.8, 132.2, 137.3, 141.6, 142.1, 151.1, 159.2, 173.7, 173.7, 173.7, 174.0, 174.7 ppm As a result of detailed examination of various physico-chemical properties and spectral data of K01-0144C substance, K01-0144C substance was determined to have the chemical structure [III] as shown hereinbefore.

Figure 13:
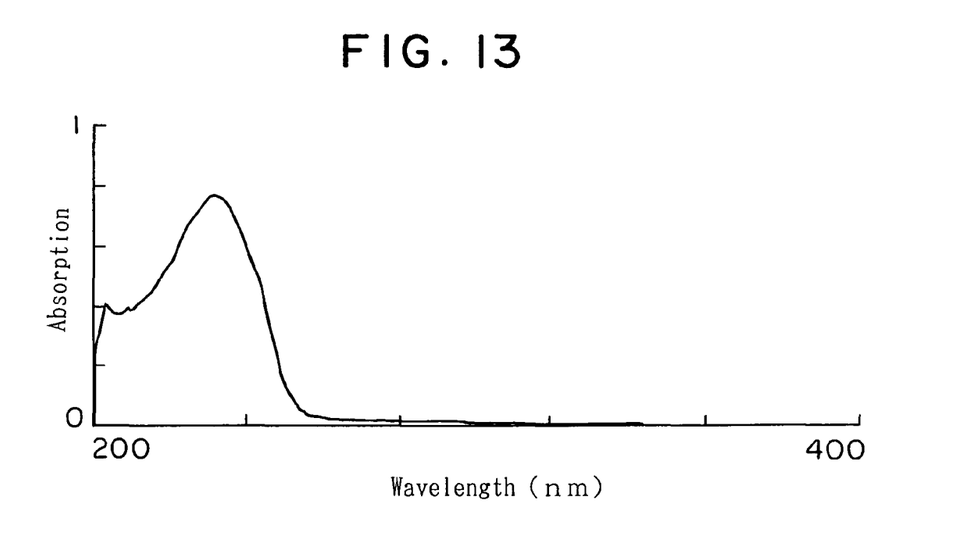
FIG. 13: U spectrum (in methanol) of K04-0144D substance
Figure 14:
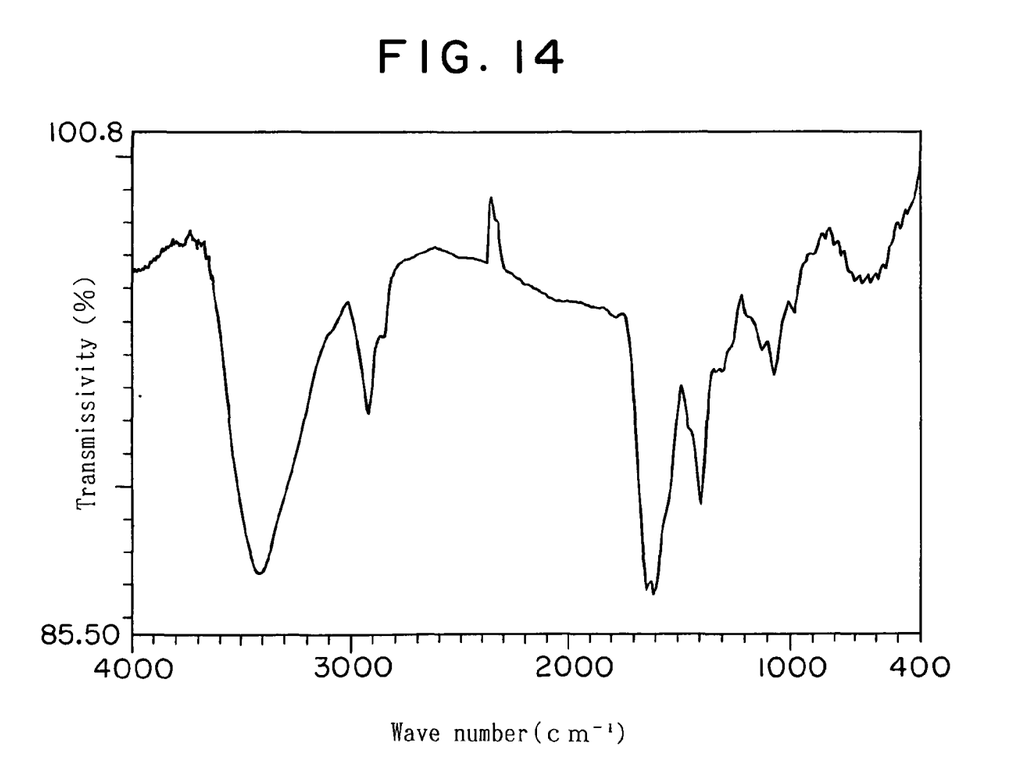
FIG. 14: IR spectrum (KBr) of K04-0144D substance
Figure 15:
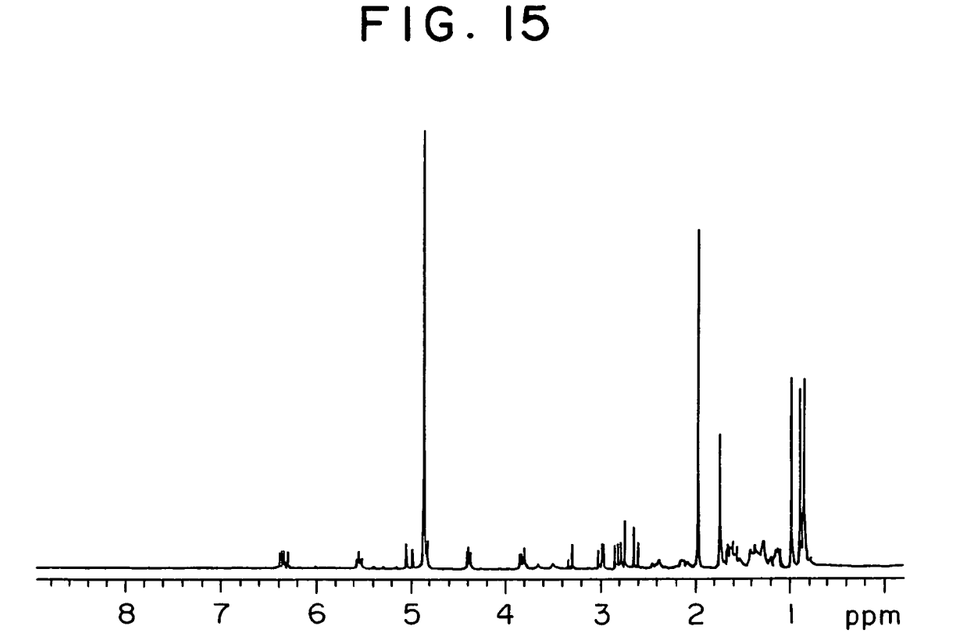
FIG. 15: Proton NMR spectrum (in deuterated methanol) of K04-0144D substance
Figure 16:
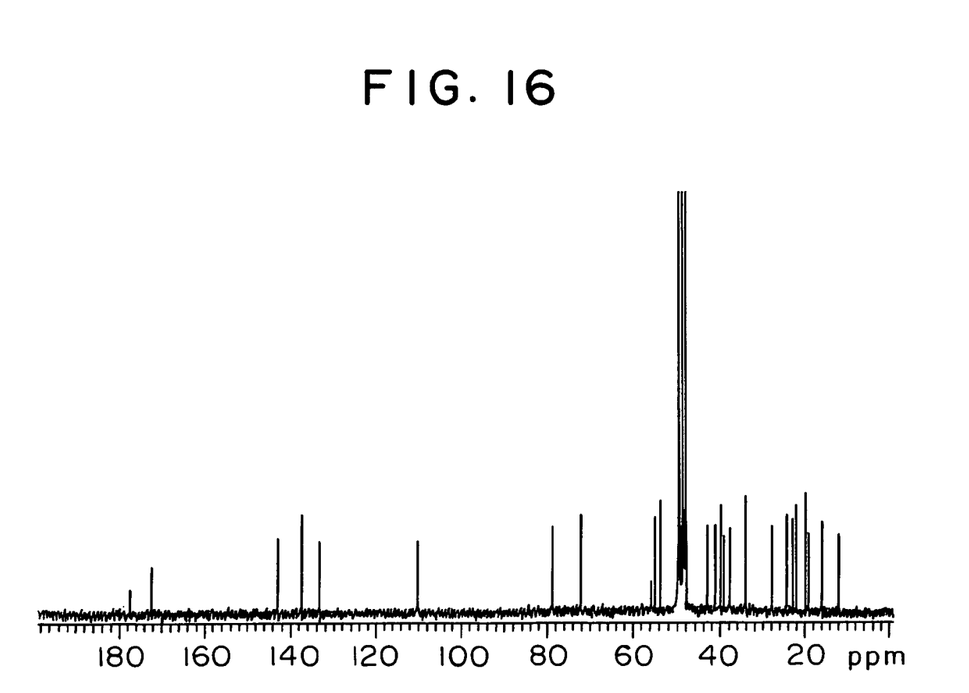
FIG. 16: Carbon NMR spectrum (in deuterated methanol) of K04-0144D substance

4. K04-0144D substance
(1) Property: white powder
(2) Melting point: 138° C.
(3) Molecular formula: $C_{25}H_{41}NO_5S$
HR FAB-MS (m/z) [M-H+2Na]$^+$: Calculated 512.2423. Experimental 512.2416
(4) Molecular weight: 467
FAB-MS (m/z) [M-H+2Na]$^+$512
(5) UV spectrum: in methanol, FIG. 13, maximum absorption 232 nm
(6) IR spectrum: KBr, FIG. 14,
Specific absorptions vmax at 3427, 2927, 2864, 1641, 1604, 1398, 1124 cm$^{-1}$ were observed.
(7) Specific rotation: $[\alpha]_D^{25}$=+26.8° (c=0.1, MeOH)
(8) Solubility in solvent:
Soluble in methanol and water acetonitrile
Insoluble in chloroform and hexane ethyl acetate
(9) Proton and carbon NMR spectra: In deuterated methanol, using Varian Inc. 400 MHz NMR spectrometer, proton NMR spectrum is shown in FIG. 15, and carbon NMR spectrum is shown in FIG. 16. Chemical shifts (ppm) of hydrogen and carbon are shown as follows.
$\delta_H$: 0.84 (5H), 0.91 (4H), 1.00 (3H), 1.14 (1H), 1.35 (2H), 1.63 (4H), 1.75 (3H), 1.98 (3H), 2.13 (1H), 2.42 (1H), 2.63 (1H), 2.77 (1H), 2.82 (1H), 3.02 (1H), 3.82 (1H), 4.41 (1H), 4.86 (1H), 5.03 (1H), 5.55 (2H), 6.35 (1H) ppm
$\delta_c$: 12.0, 16.0, 19.3, 22.3, 22.8, 24.4, 27.8, 34.0, 34.1, 37.7, 39.2, 39.8, 41.1, 43.0, 53.7, 55.2, 55.8, 72.3, 78.8, 110.1, 133.2, 137.6, 143.1, 172.5, 177.4 ppm As a result of detailed examination of various physico-chemical properties and spectral data of K01-0144D substance, K01-0144D substance was determined to have the chemical structure [IV] as shown hereinbefore.

Biological Properties:
Biological properties of K04-0144 substance of the present invention are described in detail hereinbelow. Antimicrobial activities of K04-0144A substance, K04-014.4B substance and K04-0144C substance Assay of minimum inhibitory concentration (MIC) was performed according to the agar plate dilution method (Method of Japan Society of Chemotherapy, CHEMOTHERAPY 29, 76-79, 1981).

Test organisms used were 27 types of microorganisms including clinical isolates of methicillin-resistant *Staphylococcus aureus*. Each test organism was cultured in Mueller-Hinton broth (2.1% w/v) (DIFCO) at 37° C. for 20 hours, and the cultured cells were suspended to about $10^6$ cell counts/ml in the same medium, then was used as the microbial suspension for inoculation. The prepared microbial suspension was smeared by using the microplanter on MHA medium (Mueller-Hinton broth 2.1% (w/v) and agar 1.5%) containing K04-0144A substance, K04-0144B substance or K04-0144C substance, each of which was subjected to two-fold stepwise dilution from 128 µg/ml. After culturing at 37° C. for 20 hours, MIC was determined by macroscopically confirming the growth of microorganisms. Vancomycin, arbekacin and linezolid were used as a comparative control.

Results are summarized in Table 1.

TABLE 1

Results of evaluation for activities of K04-0144A, B and C against clinical isolates (MIC)(µg/ml)

| | | substance | | | | | |
|---|---|---|---|---|---|---|---|
| | microbial strain | K04-0144A | K04-0144B | K04-0144C | vancomycin | arbekacin | linezolid |
| 1 | S. aureus FDA209P 2002.1.31 | 1 | 2 | 1 | 1 | ≦0.25 | 1 |
| 2 | S. aureus Smith 2002.1.31 | 1 | 2 | 1 | 1 | ≦0.25 | 2 |
| 3 | MRSA N315 IR94 2002.2.1 | 0.06 | 0.125 | ≦0.25 | 0.5 | 0.5 | 1 |
| 4 | MRSA N315 IR94 HR-12002.2.1 | 0.125 | 0.125 | ≦0.25 | 0.5 | 1 | 2 |
| 5 | MRSA 70 2002.2.6 | 0.06 | 0.125 | ≦0.25 | 0.5 | 0.5 | 0.5 |
| 5 | MRSA 92-1191 | 0.25 | 1 | 0.5 | 1 | 0.5 | 2 |
| 7 | S. aureus ISP447 | 0.25 | 0.5 | ≦0.25 | 1 | ≦0.25 | 2 |

TABLE 1-continued

Results of evaluation for activities of K04-0144A, B and C against clinical isolates (MIC)(μg/ml)

| | | | substance | | | |
|---|---|---|---|---|---|---|
| microbial strain | K04-0144A | K04-0144B | K04-0144C | vancomycin | arbekacin | linezolid |
| 8 S. aureus ISP217 | 0.25 | 0.5 | ≦0.25 | 1 | ≦0.25 | 2 |
| 9 S. aureus 8325(pEP2104) | 0.06 | 0.06 | 0.5 | 2 | ≦0.25 | 2 |
| 10 S. aureus 8325(pMS97) | 0.5 | 1 | 0.5 | 1 | ≦0.25 | 2 |
| 11 S. epidermidis IFO12648 2002.1.31 | 4 | 8 | 1 | 1 | ≦0.25 | 2 |
| 12 M. luteus ATCC9341 2002.1.31 | >16 | >16 | >128 | 1 | ≦0.25 | 2 |
| 13 E. faecalis ATCC21212 2002.1.31 | 1 | 2 | 0.5 | 4 | >32 | 2 |
| 14 E. facecalis NTCT12201(VanA) 2002.2.6 | 1 | 2 | 0.5 | >32 | >32 | 2 |
| 15 E. faecium NTCT12203(VanA) 2002.2.6 | >16 | >16 | 64 | >32 | 8 | 2 |
| 16 E. coli NIHJ JC-2 2002.1.31 | >16 | >16 | 8 | >32 | >32 | >32 |
| 17 C. freundii ATCC8090 2002.1.31 | >16 | >16 | 64 | >32 | 0.5 | >32 |
| 18 K. pneumoniae NCTN9632 2002.1.31 | >16 | >16 | 8 | >32 | ≦0.25 | >32 |
| 19 P. mirabilis IFO3849 2002.1.31 | >16 | 16 | 8 | >32 | 2 | >32 |
| 20 P. vulgaris OX-19 2002.2.1 | >16 | 4 | 4 | >32 | 2 | 8 |
| 21 M. morganii IID Kono 2002.2.1 | >16 | >16 | 32 | >32 | 0.5 | >32 |
| 22 S. marcescens IFO12648 2002.2.1 | >16 | >16 | 32 | >32 | 1 | >32 |
| 23 E. cloacae IFO13535 2002.2.1 | >16 | >16 | 32 | >32 | 0.5 | >32 |
| 24 E. aerogenes NCTC10006 2002.2.1 | >16 | >16 | 32 | >32 | ≦0.25 | >32 |
| 25 P. aeruginosa 46001 2002.2.1 | >16 | >16 | 32 | >32 | 1 | >32 |
| 26 P. aeruginosa E-2 2002.2.1 | >16 | >16 | 32 | >32 | 4 | >32 |
| 27 A. calcoaceticus IFO2552 2002.2.1 | 16 | 8 | 8 | >32 | ≦0.25 | >32 |

As demonstrated hereinabove, K04-0144A, B and C substances inhibited growth of Gram-positive bacteria including MRSA as equally or stronger.

Evaluation of Activities on MRSA Infectious Model Using Silkworms

As an alternative method for in vivo MRSA infection model using animals, the infection system using silkworms has been reported (Kaito et al, Microbial Pathogenesis, 32: 183-190, 2002). Effect of K04-0144A substance was measured according to this method.

Test organism used was the clinical isolate of MRSA (K24 strain). The MRSA was cultured statically using LB-10 medium (DIFCO) at 37° C. for 18 hours, and a 50 μl of the cultured strain was inoculated into the hemolymph of silkworm, 5 instar, 2nd day, (about 2 g, Ehime sansyu eggs Co., Japan). K04-0144A substance was prepared to a solution of 1 mg/ml, and 50 μl of the solution were administered by using syringe to the dorsal vessel of 5 silkworms infected with MRSA (25 mg/kg). Effect of the K04-0144A substance was evaluated by comparing the survival rate between a group with administering the sample and a group without administering the sample during the raising period of 72 hours after the inoculation. Since the silkworms without administering the sample (control) and the silkworms with administering only K04-0144A substance, 25 mg/kg, all survived at least after 72 hours, K04-0144A substance in this condition was confirmed to exhibit no toxicity against silkworms. Further, all silkworms administered with 50 μl of MRSA bacterial suspension died within 72 hours after the inoculation. Under such the condition, the silkworms administered with K04-0144A substance, 25 mg/kg, all survived after 72 hours of the inoculation. Similarly, the silkworms administered with vancomycin, 25 mg/ml, survived after 72 hours of the inoculation.

Accordingly, an efficacy of K04-0144A substance was demonstrated in the experiment with MRSA infection using silkworms.

Enhancing Action of K04-0144D Substance on Activity of Imipenem 1. Method for Evaluation of Enhancing Action on Activity of Imipenem by Paper Disc Method Clinical isolate of methicillin-resistant *Staphylococcus aureus* (MRSA) K24 strain was used as a test microorganism. After the strain of MRSA K24 was cultured in Mueller-Hinton broth (2.1% w/v) (DIFCO) at 37° C. for 20 hours, the strain was suspended to the concentration corresponding to 0.5 Mc FARAND (about $10^8$ CFU/ml) in the same medium. The suspension was smeared on MHA medium (Mueller-Hinton broth 2.1% (w/v), agar 1.5%) and a medium of the same composition containing imipenem (Tienem for Intramuscular Injection, 0.5 g, Banyu Pharmaceutical Co., Ltd., Japan) with a concentration without affecting the growth of test microorganisms, i.e. final concentration of 10 μg/ml. Smearing was performed according to the method of National Committee for Laboratory Standard, the U.S. (NCCLS), by using sterilized cotton-tipped swab (Kawamoto Sangyo Co., Ltd., Japan). Antibacterial activities against the test microorganisms on various media were indicated by a diameter of the inhibition ring with mm unit after incubation at 37° C. for 20 hours using paper disc method (thin paper disc, diameter 6 mm, ADVANTEC Inc.) Result indicated as shown in Table 2 that, under the condition using 1 μg/disc, K04-0144D substance itself did not exhibit an inhibitory ring, whereas under the condition using imipenem, an inhibitory ring with a diameter 15 mm was observed, and the enhancing action of K04-0144D substance on the activity of imipenem was confirmed.

TABLE 2

Enhancing action of K04-0144D substance on activity of imipenem using paper disc method

| | Imipenem (10 μg/ml) | |
|---|---|---|
| K04-0144D substance | (−) | (+) |
| 10 | 14 | 26 |
| 1 | — | 15 |

(μg/6 mm disc)
Diameter of inhibition ring (mm)

2. Method for Evaluation of Enhancing Action of K04-0144D Substance on Various Antibiotic Activities Using Broth Microdilution Method Enhancing action of K04-0144D substance, which exhibited potent enhancing action on activity of imipenem by using the paper disc method, on activities of other antibiotics was evaluated using a broth microdilution method. Other antibiotics used were vancomycin (Wako Pure Chemical Industries, Ltd., Japan), streptomycin (Meiji Seika Kaisha, Japan) and ciprofloxacin (Wako Pure Chemical Industries, Ltd.). Evaluation was performed by applying partially modified standard method of Japan Society of Chemotherapy (CHEMOTHERAPY 38, 103-105, 1990).

After adding 85 µl of Mueller-Hinton broth (2.1% w/v) to each well of a 96-well plate (Corning Corp., the U.S.), 5 µl of imipenem, which was previously diluted stepwise with sterilized water, was added into each well in order to maintain the final concentration from $4.8 \times 10^{-4}$ to 256 µg/ml. Further, 5 µl of the aqueous solution of K04-0144D substance were added to each well in order to maintain the final concentration of 16 µg/ml, which did not give inferior effect of K04-0144D substance itself on growth of microorganisms. After mixing well, a test microorganism MRSA was suspended to the concentration corresponding to 0.5 Mc FARAND (about $10^8$ CFU/ml). This was diluted 10-fold with adding the same medium, and 5 µl of the diluted medium were inoculated to each well. After incubation at 37° C. for 20 hours, minimum drug concentration, in which the bacterial growth was not observed macroscopically in the well, was defined as MIC. MIC with each antibiotic alone and MIC with combined use of each antibiotic and K04-0144D substance are shown in Table 3. The enhancing action on imipenem was observed in MIC with 1024-fold from 32 µg/ml to 0.03 µg/ml. Since no enhancing action was observed in vancomycin, streptomycin and ciprofloxacin, it was obvious that the activity enhancing action of K04-0144D substance was specifically effective to β-lactam antibiotics.

TABLE 3

Enhancing action of K01-0144D substance on activity of imipenem by broth microdilution method

| Antibiotics | Minimum Inhibitory Concentration (µg/ml) | | Ratio |
|---|---|---|---|
| | (−) | (+) | (−/+K04-0144D) |
| Imipenem | 32 | 0.03 | 1024 |
| Vancomycin | 1 | 1 | 1 |
| Streptomycin | 2 | 1 | 2 |
| Ciprofloxacin | 64 | 32 | 2 |

Test organism: MRSA (Clinical isolate, the Kitasato Hospital, Japan)
K04-0144D substance (16 µg/ml): ¼ concentration of minimum inhibitory concentration

BEST MODE FOR CARRYING OUT THE INVENTION

The present invention will be explained hereinbelow by mentioning example, but is not construed as limiting within the example.

Process for Production of K04-0144 Substance

1) Process for Production of K04-0144A, B and C

A strain of K04-0144 cultured on the agar slant medium (starch 1.0% (Kanto Chemical Co., Inc., Japan), NZ amine 0.3% (Wako Pure Chemical Industries, Ltd., Japan), yeast extract 0.1% (Oriental Yeast Co., Ltd., Japan), meat extract 0.3% (Kyokuto Pharmaceutical Industrial Co., Ltd., Japan), calcium carbonate 0.3% (Kanto Chemical Co., Inc., Japan) and agar 1.2% (Shimizu Shokuhin Kaisha, Ltd., Japan, adjusted to pH 7.0) was inoculated with one loopful into 500 ml Erlenmeyer flasks dispensed with 100 ml of a seed medium (starch 2.4% (Kanto Chemical Co., Inc., Japan), glucose 0.1% (Wako Pure Chemical Industries, Ltd., Japan), peptone 0.3% (Kyokuto Pharmaceutical Industrial Co., Ltd., Japan), meat extract 0.3% (Kyokuto Pharmaceutical Industrial Co., Ltd., Japan), yeast extract 0.5% (Oriental Yeast Co., Ltd., Japan) and $CaCO_3$ 0.4% (Kanto Chemical Co., Inc., Japan), adjusted to pH 6.0), and cultured at 27° C. for 3 days on rotary shaker (210 rpm). The cultured strain was inoculated 1% into 50 liters of a production medium (glucose 0.5% (Wako Pure Chemical Industries, Ltd., Japan), corn steep powder 0.5% (Maruko Co., Japan), oatmeal 1.0% (Nisshoku Co., Ltd., Japan), pharmamedia 1.0% (Iwaki & Co., Ltd., Japan), $K_2HPO_4$ 0.5% (Kanto Chemical Co., Inc., Japan), $MgSO_4 \cdot 7H_2O$ 0.5% (Wako Pure Chemical Industries, Ltd., Japan) and Trace Salt Solution 0.1% ($FeSO_4 \cdot 7H_2O$ 0.1% (Kanto Chemical Co., Inc., Japan), $MnCl_2 \cdot 4H_2O$ 0.1% (Kanto Chemical Co., Inc., Japan), $ZnSO_4 \cdot 7H_2O$ 0.1% (Kanto Chemical Co., Inc., Japan), $CuSO_4 \cdot 5H_2O$ 0.1% and $CoCl_2 \cdot 6H_2O$ 0.1% (Kanto Chemical Co., Inc., Japan), adjusted to pH 7.0) in a 90 lit. jar-fermenter and cultured at 27° C. for 6 days.

After the cultivation, the cultured liquid 50 lit. was centrifuged by using Sharpless centrifuge to separate into the supernatant and mycelia. The supernatant was charged onto the HP-20 column (φ10×20 cm, Mitsubishi Chemical Corp., Japan), washed with 1.5 lit. of water, eluted the active principle with 1.5 lit. of 100% methanol, concentrated in vacuo and freeze dried. 15 g in the thus obtained crude substance 27 g were dissolved in a small amount of water and purified by using ODS column (φ5×28 cm, Senshu Scientific Co., Ltd., Japan). After washing the ODS column with 40% methanol solution, a chromatography with a developer of a mixed solvent of methanol-purified water (2:3, 3:2, 4:1, and 100:0) was carried out. Each eluate of 4 lit. was fractionated with 40 tubes of 100 ml. The active fraction (the elution with the mixture of 3:2, from the fraction No. 4 to the fraction No. 9) was concentrated and dried to obtain brown powder substance 450 mg. This was dissolved in a small amount of methanol and was purified by using a preparative HPLC (column: PEGASIL ODS, 20φ×250 mm, Senshu Scientific Co., Ltd., Japan). A 50% aqueous acetonitrile solution (10 mM ammonium acetate, pH 3, adjusted with addition of formic acid) was used as a mobile phase, and absorption at UV 210 nm was monitored at a flow rate of 8 ml/min. Peaks showing activity at retention time 21 min., 33 min. and 37 min. were observed and collected. Collected solution was adjusted to pH 7 by adding ammonium solution and concentrated in vacuo. In addition, for the purpose of desalting, the residual aqueous solution was adsorbed to the ODS column, washed the column with water and eluted with a methanol solution. The eluate was concentrated and dried to obtain K04-0144A substance and K04-0144b substance as partially purified fractions and K04-0144C substance as an active fraction with yield 19.4 mg.

Further, K04-0144A substance and K04-0144B substance were finally purified by using the preparative HPLC (a column: PEGASIL ODS, 20φ×250 ml, Senshu Scientific Co., Ltd.). A 46% aqueous acetonitrile solution (10 mM potassium dihydrogen phosphate, pH 4.7) was used as a mobile phase, and absorption at UV 210 nm was monitored at a flow rate of 8 ml/min. A retention time of K04-0144A substance was observed at 21 minutes and K04-0144b substance was observed at 27 minutes, and these peaks were collected. The collected solution was adjusted to pH 7 by adding 10 mM aqueous potassium dihydrogen phosphate and concentrated in vacuo. In addition, for the purpose of desalting, the residual aqueous solution was adsorbed to the ODS column, washed the column with water and eluted with a methanol solution. The eluate was concentrated and dried to isolate K04-0144A substance and K04-0144b substance as the active fractions with yield 15.7 mg and 5.6 mg, respectively.

2) Process for Production of K04-0144D

The strain K04-0144 was inoculated 1% into the 90 lit. volume jar-fermenter containing 50 lit. of the same production medium as of the production of K04-0144C substance, and cultured at 27° C. for 6 days.

After the cultivation, the cultured fluid 50 lit. was centrifuged by using Sharpless centrifuge to separate into the supernatant and the mycelia. The supernatant was charged on a column HP-20 (φ20×20 cm, Mitsubishi Chemical Corp., Japan), washed with water 1.5 lit., eluted the active component with 100% methanol, dried in vacuo and freeze dried. 15 g in the thus obtained crude substance 27 g were dissolved in a small amount of water and purified by using ODS column (φ5×28 cm, Senshu Scientific Co., Ltd., Japan). After washing the ODS column with 40% methanol solution, a chromatography with a developer of a mixed solvent of methanol-purified water (2:3, 3:2, 4:1, and 100:0) was carried out. Each eluate of 4 lit. was fractionated. The active fraction (the fraction eluted with the mixture of a 4:1) was concentrated and dried to obtain brown powder substance 134 mg. This was dissolved in a small amount of methanol and was purified by using a preparative HPLC (column: PEGASIL ODS, 20φ× 250 mm, Senshu Scientific Co., Ltd., Japan). A 60% aqueous acetonitrile solution (containing 0.05% phosphoric acid) was used as a mobile phase, and absorption at UV 210 nm was monitored at a flow rate of 8 ml/min. A peak showing activity at retention time 32 min. was observed and collected. Collected solution was adjusted to pH 7 by adding 1N-aqueous sodium hydroxide solution and concentrated in vacuo. In addition, for the purpose of desalting, the residual aqueous solution was adsorbed to a column HP-20 (Mitsubishi Chemical. Co., Japan), washed the column with water and eluted with a methanol solution. The eluate was concentrated and dried to obtain K04-0144D substance and K04-0144b substance as partially purified fractions as an active fraction with yield 17.1 mg.

INDUSTRIAL APPLICABILITY

As described hereinabove, the microorganism represented by the strain K04-0144 belonging to *Streptomyces* sp. having ability to produce K04-0144 substance is cultured in the medium, and the isolated K04-0144A substance, K04-0144B substance and K04-0144C substance therefrom have strong antibacterial activities against Gram-positive bacteria including methicillin-resistant *Streptococcus* aureus (MRSA), consequently these are expected to be useful as the therapeutic agents for infectious disease caused by MRSA as well as infectious diseases caused by multidrug including β-lactam antibiotics resistant bacteria. Further, similarly, since the novel K04-0144D substance isolated from the cultured liquid has the action for enhancing the effect of β-lactam antibiotics, which are utilized as the antibacterial agents, in combination with them, it is expected to be useful as the therapeutic agent for infectious diseases caused by methicillin-resistant *Staphylococcus aureus* (MRSA) and multidrug including β-lactam antibiotics resistant bacteria.

What is claimed is:

1. An isolated compound selected from the group consisting of a compound of formula [I]:

a compound of formula [II]:

a compound of formula [III]:

and a compound of formula [IV]:

2. The isolated compound of claim 1 which is the compound of formula [I]:

3. The isolated compound of claim 1 which is the compound of formula [II]:

4. The isolated compound of claim 1 which is the compound of formula [III]:

5. The isolated compound of claim 1 which is the compound of formula [IV]:

* * * * *